United States Patent [19]

Schultz et al.

[11] 4,037,724
[45] July 26, 1977

[54] METHOD OF AND APPARATUS FOR MEASURING DEFECTS IN SEALINGS

[75] Inventors: Peter Schultz; Hinrich Martinen, both of, Quickborn, Germany

[73] Assignee: Firma Up Geratebau-und Vertriebs GmbH, Malente, Germany

[21] Appl. No.: 579,208

[22] Filed: May 20, 1975

[51] Int. Cl.² .............................................. B07C 5/342
[52] U.S. Cl. .............................. 209/111.7 R; 250/224; 356/196; 356/209
[58] Field of Search ................... 250/568, 569, 223 R, 250/224; 209/111.5, 111.7 R; 356/172, 196, 209; 73/88 A

[56] References Cited

U.S. PATENT DOCUMENTS

| | | | |
|---|---|---|---|
| 2,401,396 | 6/1946 | Wolfner | 250/572 X |
| 2,793,746 | 5/1957 | Meyer et al. | 209/111.7 R |
| 2,803,343 | 8/1957 | Dodge | 209/111.7 R |
| 3,393,800 | 7/1968 | Durand | 209/111.7 R |
| 3,629,835 | 12/1971 | Brown et al. | 250/569 |

*Primary Examiner*—Robert B. Reeves
*Assistant Examiner*—Joseph J. Rolla
*Attorney, Agent, or Firm*—Donald D. Jeffery

[57] ABSTRACT

Defects in the sealings of closures are located and measured by rotating the sealed closure and directing a light beam to the sealed area. The light beam reflected from the sealing mass is compared to a prespecified rated value and any deviation resulting from the comparison results in actuation of an ejecting device for ejecting the defective closure from the testing station.

5 Claims, 8 Drawing Figures

METHOD OF AND APPARATUS FOR MEASURING DEFECTS IN SEALINGS

BACKGROUND OF THE INVENTION

The invention relates to a method of and apparatus for measuring defects in the sealing of closures or the like, particularly of bottle caps, wherein a sealing mass is applied, in the closure area, to the base of the cap.

Container closures, for example, closures of bottles, must meet stringent requirements. The first requirement consists, independently of the shape of the closures and regardless of whether they are screw caps with a high edge or cap closures with a low edge, for example, crown cork closures, in that the closure must seal the container or the bottle, even at relatively high pressures, in a fully satisfactory manner. In carbonic acid gas-containing liquids, for example, pressures in excess of atmospheric pressure of 5 to 6 atmospheres may occur. The elastic sealing inserted in the base of the closure must therefore be faultless, at least in the closure area between the bottle edge and the inside of the closure.

The danger of a faulty sealing is always particularly great when the caps manufactured on the assembly line are not provided with punched-out sealing platelets, for example, cork discs or the like, but when the sealing is produced by the injection of a liquid sealing mass. This is due to the fact that, whereas the punched-out sealing platelets can be tested for accuracy before being inserted into the closures, and by the use of only faultless sealings a closure waste can be avoided, control in the case of the use of a liquid sealing mass can be carried out in finished caps only. The visual testing of closures, as it is presently customary in assembly lines for the closing of bottles, for accuracy in the sealing area is, however, substantially complicated for the following reasons. With the usual production speeds of about 10 caps per second, it is not possible for the human eye to cover each individual cap during a time period necessary for the control. The finished closures are therefore conveyed, in rows of about 20 pieces per row, to a slowly moving conveyer belt, so that the observer can test several caps simultaneously. At a longer observation period, however, the natural fatigue occurs, so that defects are overlooked. Since it also scarcely is possible to look vertically into the closures, the side of the cap that faces the observer, and thus the sealng area positioned at this location, is more or less concealed, depending on the height of the cap edge and on the angle of inspection relative to the cap base, so that defects occurring at this location are not discovered.

The defects existing in the sealing area may also result from too much or too little sealing mass being present in the sealing area which, in the case of bottles, is ring-shaped. While too large a sealing mass is generally not harmful since the elastic sealing, when the cap is pressed against the bottle edge, is elastically deformed and seals the bottle, it is absolutely necessary to avoid defects characterized by too little or a lack of sealing material, since the pressure can escape from the bottle at these locations.

SUMMARY OF THE PRESENT INVENTION

The aim of the invention consists therefore in producing a method and apparatus for measuring defects in the sealing of closures, by means of which the aforementioned disadvantages of the conventional control methods are avoided and a fast and safe discovery of sealing defects in the closures becomes possible. The apparatus is, furthermore, constructed in such a way that caps provided with faulty sealings are automatically ejected.

The invention consists in conveying the cap to a control apparatus and setting it in rotary motion. A light beam covering the width of the sealing area is introduced and directed toward the cap base covered with the sealing mass. The light beam reflected from the sealing mass or from the cap base uncovered due to a faulty distribution of the sealing mass, is intercepted and compared to a prespecified rated value. In the apparatus, the advantageous provision is made that a measuring value that deviates from the rated value is utilized to control a machine, specifically an ejection device, which reacts only when a cap with a faulty sealing is discovered.

The invention, furthermore, is characterized by a device provided with a light source an image of which is formed by means of an optical system, especially a mirror and/or lens system, on the sealing mass in the sealing area of the rotating cap, and which is provided with a detector having an ejecting device, which detector measures the intensity of the light beams reflected by the cap and controls the ejecting device according to a rated value comparison.

The invention utilizes the fact that defects characterized by too little or a lack of material in the sealing area, due to the diversified surface conditions, result in diversified surface reflection properties which are discovered by the optical detector. When, in a comparison to a reflection rated value prespecified for a specific sealing mass, a different measuring value results, the detector furnishes an output signal which actuates the ejection device and ejects the cap from the assembly line.

According to a preferred embodiment of the apparatus of the invention for measuring the locations of defects in the sealing, a first lens device is provided which bundles the beams emitted by the light source and forms an image of the light source on the sealing mass in the sealing area of the rotating cap, and a second lens device may be provided which bundles the light beams reflected by the cap, and images the image of the light source located on the cap, in the detector. The path of beams from the light source, and the path of beams reflected by the covered cap base to the detector are therefore separated from each other.

According to a further preferred embodiment of the apparatus of the invention, a first lens device is provided which conducts the beams emitted by the light source to a semitransparent mirror, as well as a second lens device which bundles the beams reflected by the mirror and images the light source on the sealing mass in the sealing area of the rotating cap, and a third lens device is provided which bundles the beams reflected by the cap behind the semitransparent mirror, and images the image of the light source located on the cap, in the detector. In place of the three lens devices, an embodiment with one lens only is conceivable which is arranged between the semitransparent mirror and the sealing surface to be controlled, in which arrangement the image points of the light source and of the detector on the sealing area coincide. The light source and the detector are in this case displaced into the corresponding points of image. It is also imaginable that in place of the semitransparent mirror other beam divider arrangements are employed, for example, several mirrors plus a semitransparent mirror, beam divider prisms, or the like.

The advantage of the apparatus above described consists in that a vertical inspection direction is made possible, so that the path of beams through the cap edge is not affected and even sealing areas directly located in the cap corner are covered. By the selection of a suitable focal length of the lens a path of beams without losses of light (except beam divider losses) can be obtained by means of which sealing areas located in the cap corner can also be reached.

According to a further preferred embodiment of the invention, the light source is optically coupled with a first fiber-optical photoconductor which forms an image of the light source on the sealing mass in the sealing area of the rotating cap, and a second fiber-optical photoconductor optically coupled with the detector is provided which forms an image of the image of the light source located on the cap in the detector. By means of this arrangement a similar practically vertical inspection direction is achieved, so that the cap edge cannot exert an influence upon the measuring values.

The control of the ejecting device is carried out by the detector whenever a reflection intensity that deviates from the rated value is measured by the detector. For this purpose the detector is connected to the ejecting device through an amplifier, an amplitude discriminator, a gate stage and a terminal stage.

According to a further advantageous characteristic of the invention, the light source emits constant light of constant intensity or pulse light with constant intensity amplitude. In this operation the pulse train is advantageously adapted to the speed of rotation of the sealing area, so that a continuous scanning of the sealing area takes place.

A still further advantageous characteristic of the invention is that the light emanating from the light source has a wave length $\lambda$ at which the relative reflection factors of the sealing material and the cap underlying base differ as much as possible. Should a wave length of the light emanating from the light source be chosen in the range of which the reflection factors of the materials used exhibit no or only a small difference, a detection of defects would not be possible.

In an advantageous manner the detector presents at the chosen wave length of the beams emanating from the light source its maximum sensitivity. The sealing area, according to the invention, is therefore illuminated by a more or less monochromatic light with a wave length adapted to the materials to be tested, and the beams reflected by the sealing mass or the cap material, respectively, are picked up by the detector which at these wave lengths presents its maximum sensitivity.

Advantageously, the image of the light source on the sealing mass in the sealing area of the rotating cap is formed in the form of a point or a line, in which image the diameter of the point or the length of the line corresponds at least to the width of the sealing area. This dimensioning of the light beam presents the advantage that the light is concentrated onto the area to be controlled, so that the loss of illumination intensity at a prespecified intensity of radiation of the illuminating device is kept to a minimum. The bundling of the light beams to a point or line can be carried out much more simply than a circular illumination of an area which requires installation of suitable diaphragms or the like which suffer from heavy light losses.

However, in order to scan the entire circular ring, provision is made, according to a further characteristic of the invention, that the cap be rotated during the time of measurement, in which operation the angle of rotation amounts at least to 360°, preferably a multiple of 360°, so that the reliability of the measurement increases.

In the case in which the path of the beams emanating from the light source and the path of the beams reflected toward the detector are separated, it is advantageous to take care that the angle of incidence $\alpha$ of the path of beams introduced into the cap equal with relation to the cap base the angle of reflection $\beta$ of the reflected path of beams emanating from the cap, and are smaller than than 90°.

When the wavelength $\lambda$ of the light emanating from the light source is chosen in such a way that the light ranges in the non-visible spectrum, the adjusting device provided by the invention serves to set the point of measurement on the sealing surface to be measured. The adjusting device is advantageously formed by a second light source radiating in the visible area and arranged in the lateral area of the detector or the light source, which second light source is pivotable into the optical axis of the optical system. This auxiliary light source may be advantageously connected to the detector or the measuring light source by means of a disc or a rotating device in such a manner that by a simple displacement of the disc or a rotation of the rotating device the auxiliary light source assumes the position of the detector or the measuring light source.

Further characteristics, advantages, and details of the invention will be apparent from the specification which follows in particular reference to the application drawings.

BRIEF DESCRIPTION OF THE APPLICATION DRAWINGS

DETAILED DESCRIPTION OF THE PREFERRED EMBODIMENTS

Figure 1:
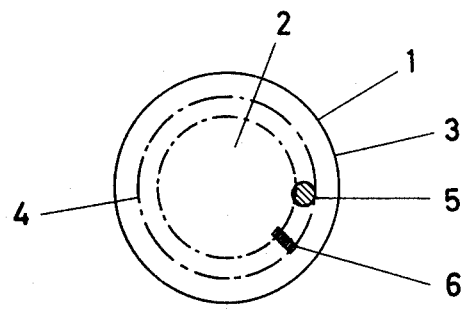
FIG. 1 is a plan view of a cap to be controlled, with a light point or light line focused thereon.

Referring now in more detail to the application drawings wherein like parts are indicated by like reference numerals, the cap 1 shown in FIG. 1 is shaped as a cylindrical body with a base 2. While the cap for the purpose of its use as a screw cap is provided with a relatively high edge 3, the edge in the generally employed crown cork closures is relatively low.

To produce a sealing, base 2 of cap 1 is coated on its interior surface with an elastic sealing mass which is introduced into the cap in a liquid state and is uniformly distributed over the cap base 2 by a rotation of the cap under the effect of centrifugal force. The sealing area 4 wherein base 2 of cap 1 abuts against the upper bottle edge is shown in dot and dash lines in FIG. 1. Depending on the shaping of the bottle neck, the sealing area is located more or less close to the edge of the cap and is more or less wide. Since the bottles frequently contain carbonic acid gas-containing liquids, the sealing surface must be faultless and a fully satisfactory sealing, even against relatively high pressures, must be assured.

FIG. 1 shows a light point 5 imaged on cap base 2, with the diameter of the point 5 being somewhat larger than the width of the sealing area 4. In place of the light point 5, a light line 6 may also be focused in, with the length of the line 6 likewise somewhat larger than the width of the sealing area. Since the point or the line does not change its relative position with respect to the cap, the cap must be rotated, so that the ring-shaped sealing area is completely scanned by the light point or the light line.

The sealing area is essentially illuminated only in the width or region of the circular ring 4 since defects outside the circular ring are immaterial and do not affect the sealing of the bottle. Besides, with an increase in the size of the illuminated surface at a prespecified radiation intensity of the illuminating device the intensity of illumination decreases quadratically.

Figure 2:
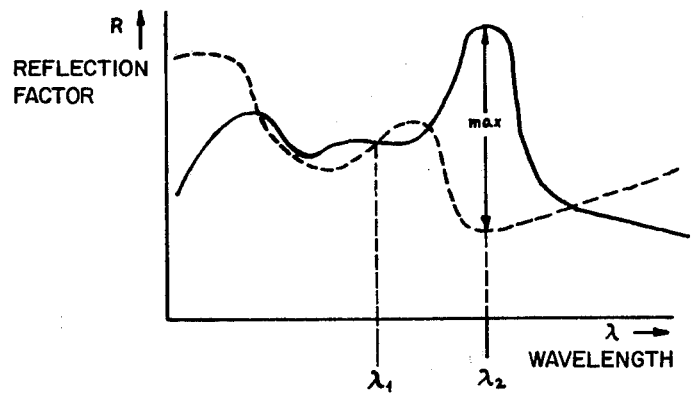
FIG. 2 is a diagrammatic view wherein the reflection factor of two work materials is applied over the wave length of the beamed-in light.

In the basic diagram shown in FIG. 2, the reflection factors of two different materials are recorded in relative units along the wave lengths of the entering light $\lambda$. The solid line is to diagrammatically illustrate the progress of the reflection conduct of the sealing mass, and the dash line is to illustrate diagrammatically the progress of the reflection conduct of the cap material. It can be recognized that at various points there are intersections and larger distances between the reflection curves. If a light source were chosen whose wave length would amount to $\lambda_1$, a defect in the sealing would not be discovered since both work materials at this light wave length present the same reflection conduct. It is therefore suitable to select a light source whose light presents a wave length $\lambda_2$ since in this case the deviation in the reflection conduct is largest. In order to obtain reliable measuring value results, the detector should have a sensitivity as high as possible at the selected wave length $\lambda_2$.

Figure 3:
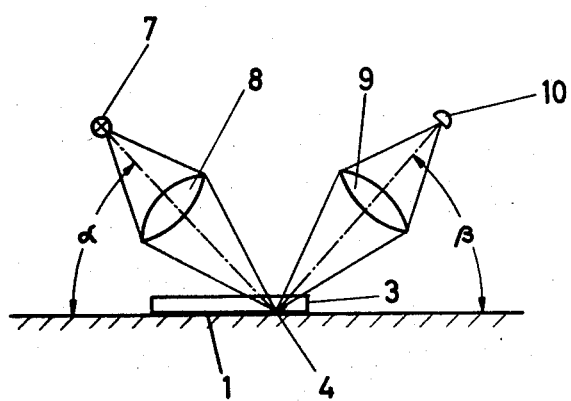
FIG. 3 is a diagrammatical view of an embodiment of the apparatus of the invention with separated paths of beams.

FIG. 3 shows a diagrammatical representation of an embodiment of the apparatus of the invention by means of which the locations of defects in the sealing area can be optically discovered. A light source 7 is imaged on sealing area 4 of cap 1 by way of a lens device 8. By means of a second lens device 9 the beams reflected by cap 1 are bundled, and the image of light source 7 located on the cap is imaged in a detector 10. The angle of incidence $\alpha$ of the entering light corresponds to the angle of reflection $\beta$ of the reflected light and is smaller than 90°. The angles are delimited by the height of edge 3 of cap 1. In the selection of the angles the greatest care possible should be taken that the entire light entering the cap is reflected by the sealing area to be controlled and be collected in the detector.

Figure 4:
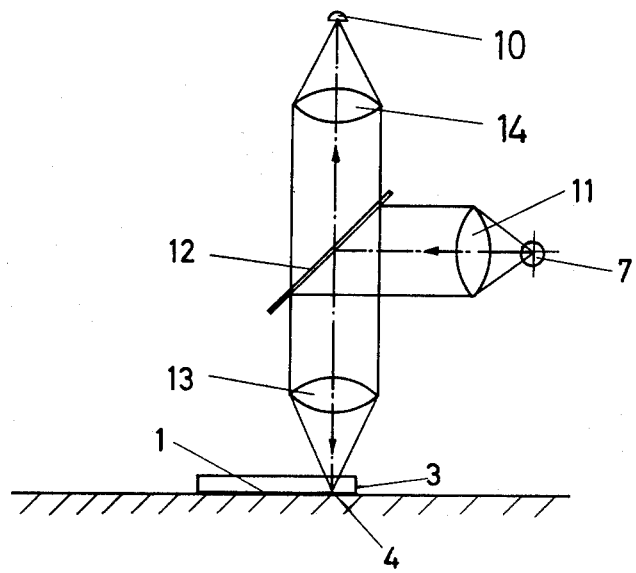
FIG. 4 is a diagrammatical view of an alternative embodiment of the apparatus of the invention with a joined path of beams.

The embodiment of the apparatus of the invention diagrammatically represented in FIG. 4 is provided with a first lens device 11 by means of which the beams emanating from light source 7 are directed upon a semitransparent mirror 12. A portion of the beams emanating from light source 7 is reflected downward by the mirror 12 and imaged as a point by means of a second lens device 13 on the sealing area 4 of cap 1. The beams reflected vertically upwardly penetrate the semitransparent mirror 12 and are bundled behind the mirror by means of a third lens device 14 in such a manner that the image of light source 7 located on cap 1 is imaged in detector 10.

Figure 5:
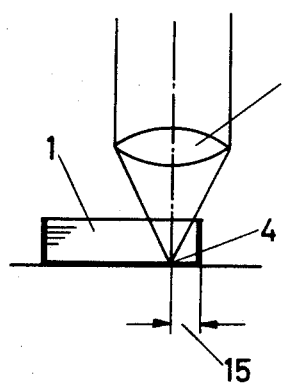
FIG. 5 is a partial view of the apparatus according to FIG. 4 with a lens device of a short focal length.
Figure 6:
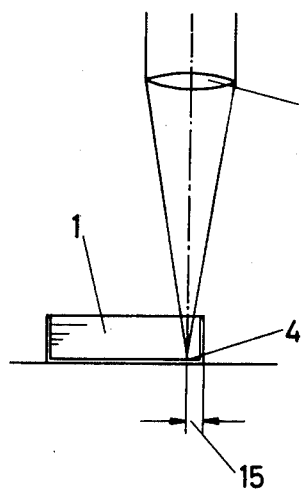
FIG. 6 is a partial view of the apparatus according to FIG. 4 with a lens device of a long focal length.

As can be recognized in FIGS. 5 and 6, it is possible to achieve by a suitable selection of lens 13a or 13b a vertical path of beams by means of which sealing areas at varying distances 15 from the edge 3 of cap 1 can be scanned.

Figure 7:
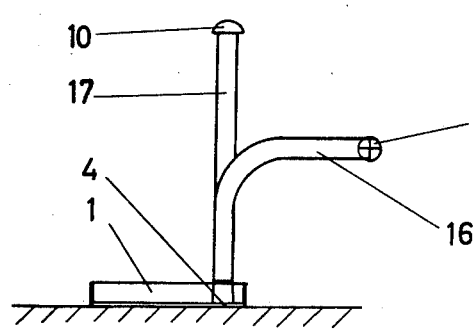
FIG. 7 is a diagrammatical view of a further embodiment of the apparatus of the invention with joined paths of beams.

In place of the lens and mirror systems of the devices shown in FIGS. 3 and 4, photoconductors 16, 17 may also be employed according to the embodiment of FIG. 7, in which case a photoconductor 16 is optically coupled with light source 7 and images the light source on the sealing mass in the sealing area 4 of rotating cap 1. The other photoconductor 17 is optically coupled with detector 10 and conducts the image of light source 7 located on cap 1, in the detector. This arrangement likewise permits a practically vertical direction of inspection without the occurrence of losses caused by an edge cover of the cap.

Figure 8:
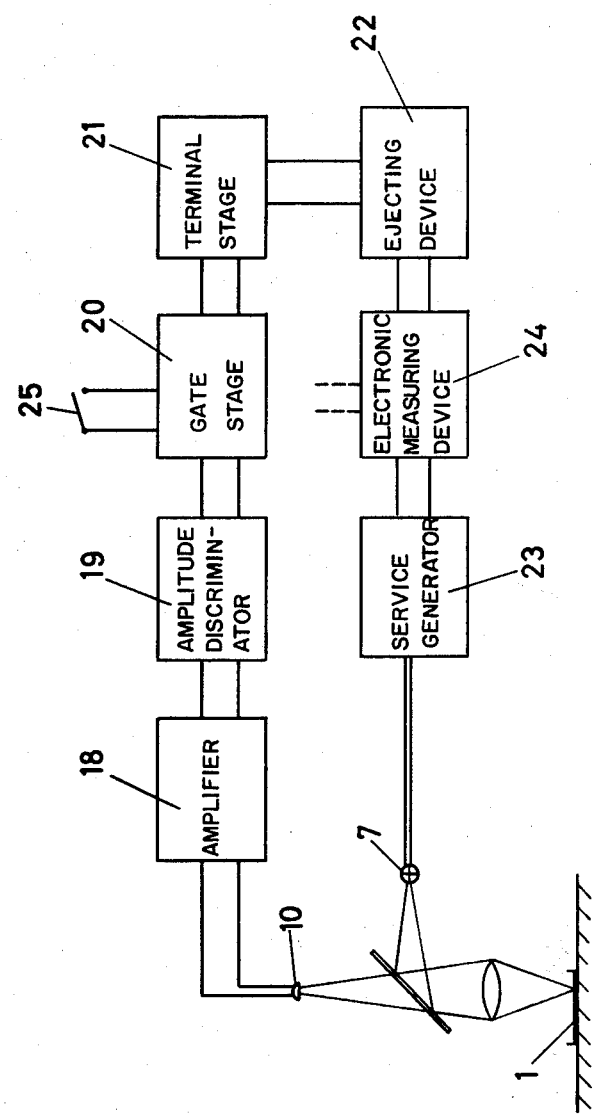
FIG. 8 is a diagrammatic view of the system which includes the electronic measuring device.

FIG. 8 shows in diagram the structure of the electronic measuring device. It can be recognized that detector 10 is connected to an ejecting device 22 by way of an amplifier 18, an amplitude discriminator 19, a gate stage 20, and a terminal stage 21. Light source 7 is supplied with current by means of a service generator 23 which in turn is connected to the current supply source of an electronic measuring device 24.

The operation of the measuring device of the invention will be described. Cap 1 rotates about the center of the circular-ring-shaped sealing area 4. During this operation the reflection factor is measured along the width of sealing area 4 and the entire periphery thereof. The light source 7 used for illumination may emit either constant light of constant intensity or pulse light of constant intensity amplitude. In the latter case the pulse train must be adapted to the speed of rotation of the sealing area so that a continuous scanning of the sealing area is assured. Detector 10 measures during this operation the intensity of the light reflected by the sealing area. When a deviation from the rated value prespecified for a fully satisfactory sealing area is discovered, ejection device 22 is actuated by means of an electronic measuring device, which ejecting device may comprise or include, for example, a magnetic valve. The objectionable cap is removed by the ejecting device from the assembly line.

The signal transmitted by the detector is amplified by the amplifier 18 and in the amplitude discriminator 19 the amplified signal amplitude is compared with a previously adjustable rated amplitude. When a deviation from the rated value is found, an active switch element is actuated, whereby an auxiliary current circuit is switched on or off. This circuit, however, is also controlled by a gate stage for example, by means of a switch. The measuring process proper does not take place continuously but periodically during the time period at which the cap has reached its rated speed of rotation and carries out one or more rotations at this speed. This period of time is determined by means of a switch 25, and the apparatus exerts the effect in the gate stage 20 that a possible ejecting signal is transmitted to the terminal stage 21 during this period of time only. The terminal stage 21 then switches the ejecting device 22.

The control of the measuring moment as well as of the duration of the measuring can be carried out in principle by means of the gate stage, in all groups of the circuit, so that, for example, the light source controlled by the gate stage operates only during the duration of the measurement. Likewise, the detector, the amplifier, the amplitude discriminator, the terminal stage, and the ejecting device can be activated, by way of the gate stage, during the duration of the measurement only.

We claim:

1. A method for measuring sealing material defects in a circular, ring-shaped sealing area of a container closure, said sealing area being located on the bottom, interior surface of an axially symmetrical closure, and said sealing area being coated with a sealing material, said sealing material having a different coefficient of reflectivity of light than said bottom interior surface at a predetermined wavelength, comprising the steps of:
   a. selecting a wavelength such that there is a maximum difference between the reflectivity coefficients of said sealing material and said bottom interior surface of said closure,
   b. positioning said closure in a predetermined control area;
   c. illuminating a predetermined scan area of said sealing area of said closure with substantially monochromatic light pulses of said predetermined wavelength, the width of said predetermined scan area corresponding to the annular width of said sealing area;
   d. maintaining said light pulses at a constant amplitude and correlating the pulse rate of said pulsed light to the rotational speed of said closure whereby an unbroken scanning of said sealing area is carried out,
   e. detecting the level of the light of said predetermined wavelength reflected from said predetermined scan area;
   f. rotating said closure by at least 360° about the axis of said ring-shaped sealing area so that the light reflected from said sealing area is progressively scanned over said entire sealing area;
   g. comparing said detected light level with a predetermined value representing the reflected light level of an inadequately coated portion of said sealing area; and
   h. ejecting said closure from said predetermined control area when said detected light level corresponds to said predetermined value, whereby closures having a defect in said sealing material coating over a portion of said sealing area are rejected prior to being applied to a container.

2. The method of claim 1, wherein the step of rotating said closure about the axis of said sealing area further comprises rotating said closure by a multiple of 360° while said sealing material defects are being measured.

3. The method of claim 1, wherein the step of illuminating said predetermined scan area further comprises arranging the angle of incidence of the path of light rays introduced into the closure with respect to the bottom, interior surface of said closure at an angle smaller than 90°.

4. The method of claim 1, wherein the step of illuminating substantially only a predetermined scan area of said sealing area with monochromatic light of said predetermined wavelength comprises further, when said predetermined wavelength is in the non-visible range of light, the steps of:
   illuminating said predetermined scan area with a visible light source in order to determine the proper position of a light source for illuminating substantially only said predetermined scan area; and
   substituting said monochromatic light source of said predetermined wavelength for said visible light source, whereby said predetermined area is illuminated by said monochromatic light of said predetermined wavelength.

5. An apparatus for measuring sealing material defects in a circular, ring-shaped sealing area of a container closure, said sealing area being located on the bottom, interior surface of an axially symmetrical closure and said sealing material having a different reflectivity coefficient of light than said bottom, interior surface at a predetermined wavelength, said predetermined wavelength being selected such that there is a maximum difference between the reflectivity coefficients of said sealing material and said bottom, interior surface, comprising:
   a. means for positioning said closure in a predetermined control area;
   b. means for illuminating substantially only a predetermined scan area of said sealing area with a light of said predetermined wavelength, the width of said predetermined scan area corresponding to the annular width of said ring-shaped sealing area, said illuminating means comprising a pulsating light source having pulses of constant intensity amplitude, the pulse frequency of said pulsating source being correlated to the closure rotation speed of said rotating means, whereby an unbroken scanning of said sealing area is effected;
   c. means for detecting the level of the light of said predetermined wavelength reflected from said predetermined scan area;
   d. means for rotating said closure by at least 360° about the axis of said ring-shaped sealing area so that the light reflected from said sealing area is progressively scanned over said entire sealing area;
   e. means for comparing said detected light level with a predetermined value representing the reflected light level of an inadequately coated portion of said sealing area; and
   f. means for ejecting said closure from said predetermined detection area when said detected light level corresponds to said predetermined value representing the reflected light level of an inadequately coated portion of said sealing area, whereby closures having defects in said sealing material coating over a portion of of said sealing are rejected prior to being applied to a container.

* * * * *